(12) United States Patent
Isikman et al.

(10) Patent No.: US 9,851,298 B1
(45) Date of Patent: Dec. 26, 2017

(54) LIGHT-BASED SHIELDING DETECTION

(71) Applicant: Apple Inc., Cupertino, CA (US)

(72) Inventors: Serhan O. Isikman, Sunnyvale, CA (US); Brian R. Land, Woodside, CA (US); Erno H. Klaassen, Los Altos, CA (US)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 15/271,002

(22) Filed: Sep. 20, 2016

Related U.S. Application Data

(60) Provisional application No. 62/233,133, filed on Sep. 25, 2015.

(51) Int. Cl.
| | | |
|---|---|---|
| *G01J 5/02* | (2006.01) | |
| *G01N 21/47* | (2006.01) | |
| *G01N 33/00* | (2006.01) | |

(52) U.S. Cl.
CPC ............ *G01N 21/47* (2013.01); *G01N 33/00* (2013.01); *G01N 2033/0096* (2013.01)

(58) Field of Classification Search
CPC .... G01N 21/3563; G01N 21/55; G01N 21/84; G01N 2201/8472; G01N 2201/1293; G01N 2201/021; G01N 2201/129; G01J 1/4204; G01J 1/4228; G01J 2001/4266
See application file for complete search history.

(56) References Cited

U.S. PATENT DOCUMENTS

| | | | |
|---|---|---|---|
| 5,483,261 A | 1/1996 | Yasutake | |
| 5,488,204 A | 1/1996 | Mead et al. | |
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,310,610 B1 | 10/2001 | Beaton et al. | |
| 6,323,846 B1 | 11/2001 | Westerman et al. | |
| 6,690,387 B2 | 2/2004 | Zimmerman et al. | |
| 7,015,894 B2 | 3/2006 | Morohoshi | |
| 7,184,064 B2 | 2/2007 | Zimmerman et al. | |
| 7,616,110 B2 | 11/2009 | Crump et al. | |

(Continued)

FOREIGN PATENT DOCUMENTS

| | | |
|---|---|---|
| JP | 2000-163031 A | 6/2000 |
| JP | 2002-342033 A | 11/2002 |

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

(Continued)

*Primary Examiner* — Kiho Kim
(74) *Attorney, Agent, or Firm* — Morrison & Foerster LLP

(57) ABSTRACT

Disclosed herein is a sunscreen detector for use with portable device, such as a mobile and/or wearable device. One variation of a sunscreen detector comprises an illumination system that is configured to illuminate a target skin area with ultraviolet and/or infrared spectrum light and a sensor system that is configured to detect the amount of ultraviolet and/or infrared spectrum light that is reflected from the target skin area. The sunscreen detector is configured to analyze the data collected by the sensor system to generate a notification to the user as to whether they should apply sunscreen.

20 Claims, 8 Drawing Sheets

(56) References Cited

U.S. PATENT DOCUMENTS

| | | | |
|---|---|---|---|
| 7,663,607 | B2 | 2/2010 | Hotelling et al. |
| 8,378,811 | B2 | 2/2013 | Crump et al. |
| 8,479,122 | B2 | 7/2013 | Hotelling et al. |
| 8,618,930 | B2 | 12/2013 | Papadopoulos et al. |
| 9,173,570 | B2 | 11/2015 | Millikan |
| 2006/0197753 | A1 | 9/2006 | Hotelling |
| 2008/0161661 | A1* | 7/2008 | Gizewski ............ A61B 5/0059 600/306 |
| 2009/0095906 | A1* | 4/2009 | Gavner ............ H04N 1/00307 250/338.1 |
| 2009/0321647 | A1* | 12/2009 | Shelley ............ G01N 21/3563 250/339.07 |
| 2010/0198026 | A1 | 8/2010 | Young et al. |
| 2014/0155705 | A1 | 6/2014 | Papadopoulos et al. |
| 2015/0102208 | A1 | 4/2015 | Appelboom et al. |
| 2015/0338272 | A1 | 11/2015 | Rastegar et al. |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI ' 92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

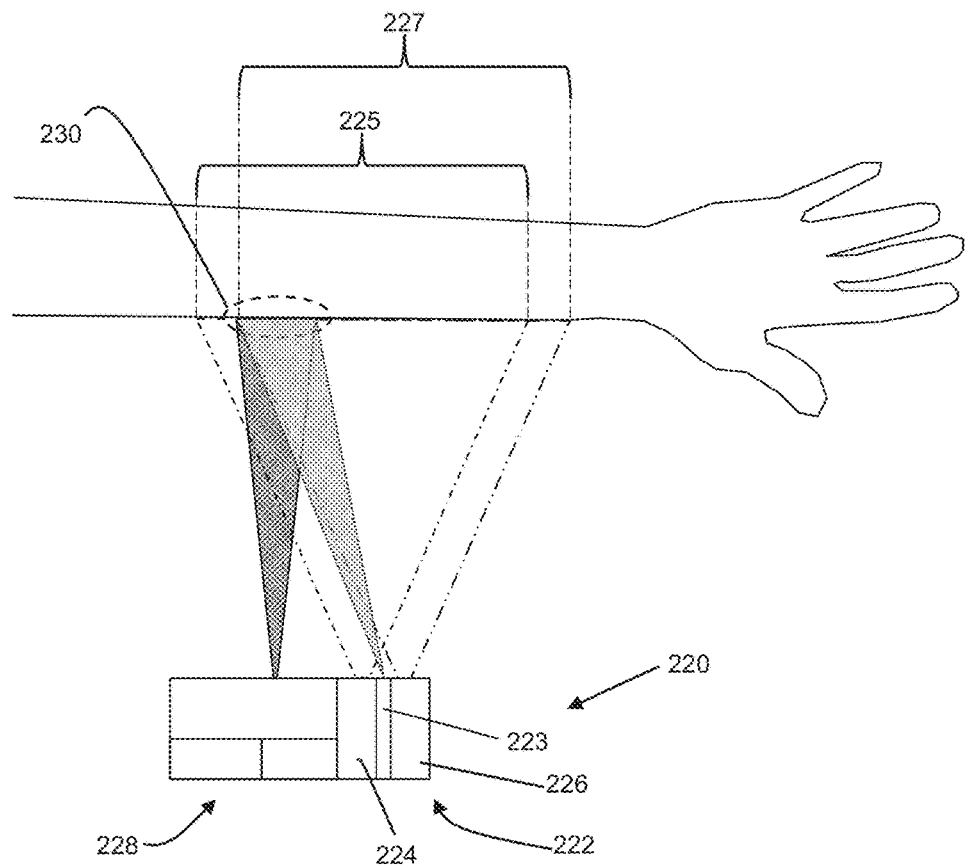
FIG. 2B
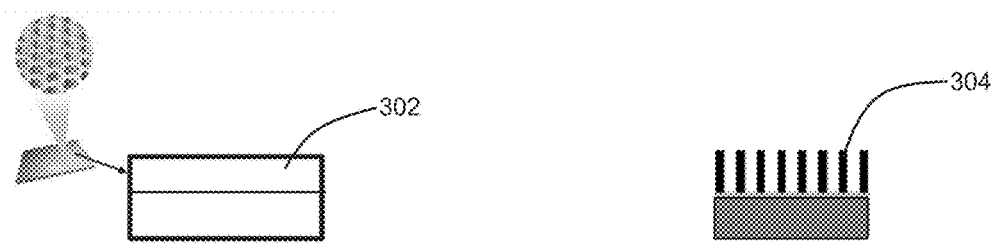
FIG. 3A
FIG. 3B

LIGHT-BASED SHIELDING DETECTION

CROSS-REFERENCE TO RELATED APPLICATIONS

This application claims priority to U.S. Provisional Patent Application Ser. No. 62/233,133 filed Sep. 25, 2015, which is hereby incorporated by reference in its entirety.

FIELD

This relates generally to light sensors included in electronic devices and methods for measuring one or more signals using the light sensors. More specifically, this disclosure relates to a UV-IR spectrometer and methods for detecting light-based shielding.

BACKGROUND

Overexposure to ultraviolet (UV) radiation can be associated with a variety of health conditions. Risks for some of the health conditions can correspond to a person's natural sensitivity to UV exposure and the lifetime UV exposure from both sunlight and artificial sources (e.g., tanning beds and tanning lamps). In addition, physical characteristics (e.g., hair color, eye color, and/or skin color) can be correlated with the risk of skin-related health conditions. Protective measures (e.g., staying indoors or in the shade during peak times during the day, and use of protective clothing) can be taken to reduce the risks of UV overexposure to the skin. Protective measures can also include the application of sunscreen to potentially exposed areas of skin. Although sunscreen can be characterized based on sun protection factor (SPF), the efficacy of the sunscreen as applied to the user's skin may differ based on, for example, the breakdown of one or more active ingredients in the sunscreen can break down, the user's skin sensitivity, the sunscreen's water-resistance.

BRIEF SUMMARY

The application of sunscreens prior to sun exposure may help to block UV radiation using a combination of one or more active ingredients. Inorganic particles (e.g., titanium dioxide or zinc oxide) may act as a physical sunblock to physically deflect UV light by forming a physical barrier that reflects or scatters UV rays. Organic components (e.g., avobenzone, octyl methoxycinnamate (OMC) or oxybenzone) may act to absorb UV rays/radiation so that they are not absorbed by the skin. These organic ingredients can slowly break down and release the energy from the absorbed UV rays as heat. Sun Protection Factor (SPF) is a metric that indicates how well the sunscreen protects against UVB radiation. The SPF number refers to roughly how long it will take for average person's skin to turn red (e.g., how long you can stay in the sun before getting sunburn), and is a multiplication factor that indicates how much longer a sunscreen lotion augments the skin's natural ability to resist sunburn. For example, sunscreen with an SPF of 15 will prevent skin from getting red for approximately 15 times longer than usual. That is, if a person's skin starts to burn after 10 minutes of sun exposure, sunscreen with SPF 15 will increase that time period by a factor of 15, and prevent sunburn for about 150 minutes, or 2.5 hours. However, the identified SPF may not be accurate, and may be affected by other factors, including water-resistance. Although sunscreen lotions labeled as being capable of blocking both UVB and UVA radiation, there is currently no standard metric that indicates UVA blocking efficacy.

Disclosed herein is a UV-IR spectrometer for mobile and/or wearable devices. The UV-IR spectrometer may be a sunscreen detector that is configured to identify the degree of sunscreen coverage in exposed areas of the skin of a user or subject and may provide information about regions that may be at elevated UV exposure risk. The sunscreen detector may be configured to indicate areas of skin or entire body parts where sunscreen protection is missing or inadequate. Based upon the detected sunscreen coverage, the detector may provide notifications or instructions to the user about where to apply or re-apply sunscreen, and/or how much and how often to apply sunscreen.

For example, the detector may be configured to identify exposed skin based upon infrared light reflection, and the degree of reflected or absorbed ultraviolet light detected in the exposed skin areas to determine the degree sunscreen coverage. The sunscreen detector may also identify exposure risk relating to the user's physical attributes, their anticipated sun exposure, and activity. In some variations, the detector may make recommendations relating to use of sunscreen having a minimum SPF, and/or recommendations relating to the frequency of application.

The UV-IR spectrometer may comprise a controller that is configured to provide notifications to the user of insufficient UV light protection, encouraging the user to re-apply sunscreen. For example, the UV-IR spectrometer may be used when sunscreen is initially applied and may alert the user if the quantity of lotion or skin coverage of the lotion is insufficient. The spectrometer may also be used to remind the user to re-apply sunscreen after the initial application, so that the user can re-apply new sunscreen before the older sunscreen has depleted its UV blocking capabilities. This UV-IR spectrometer may provide the user with actionable information so that they can proactively protect their skin in order to help prevent skin-related health conditions.

One variation of a UV-IR spectrometer that may be a sunscreen detector may comprise an illumination system configured to emit UV spectrum light and IR spectrum light, a sensor system configured to detect UV spectrum light and IR spectrum light at a sensor field, and a controller configured to receive a UV signal and an IR signal from the sensor system and to output a first output signal when the IR signal is above an IR threshold and the UV signal is below a UV threshold. The illumination system may comprise a UV illumination field and an IR illumination field and the sensor field may be located within the UV illumination field and the IR illumination field. The sensor system may comprise an optic to limit the sensor field. The optic may be a fiber-optic faceplate, or a diffraction optic, or a low numerical-aperture hole array. The sensor field may have an effective field of view in the range of 5 degrees to 180 degrees, or 15 degrees to 135 degrees, or 30 degrees to 90 degrees, for example. In other embodiments, the sensor field may be characterized as an area in the range of 0.1 to 1500 cm$^2$ at a distance of 5 cm from the sensor system, and in some variations, the sensor field may have an area in the range of 0.5 to 20 cm$^2$ at a distance of 5 cm, or 1 to 15 cm$^2$ at a distance of 5 cm from the sensor system. In some variations, the sunscreen detector may comprise a sensor module, and the illumination system and the sensor system may be located on the sensor module. The sensor module may be located in a portable multifunction device, such as a cell phone, or a watch, including but not limited to a band of a watch. The controller may be configured to overlay a graphic corresponding to the sensor field onto a camera image. For example, the graphic may be a first graphic corresponding to the first output signal. The controller may be further configured to output a second output signal when the IR signal is above an IR threshold and the UV signal is above a UV threshold, and the graphic may be a second graphic corresponding to the second output signal. The controller may also be configured to output a third output signal when the IR signal is below an IR threshold, and the graphic may be a third graphic corresponding to the third output signal. Optionally, the illumination system may be further configured to emit visible light. Some variations of a sunscreen detector may also comprise a distance sensor system configured to detect an object distance of an object in the sensor field from the distance sensor system. For example, the distance sensor system may be a Doppler sensor system.

Also disclosed herein is a method for detecting sunscreen coverage. One variation of such a method may comprise positioning a sunscreen detector over a target skin region, where the sunscreen detector comprises an illumination system configured to emit UV spectrum light and IR spectrum light, a sensor system configured to detect UV spectrum light and IR spectrum light at a sensor field located within the UV illumination field and the IR illumination field, and a controller configured to receive a UV signal and an IR signal from the sensor system, moving the sunscreen detector across the target skin region, emitting and sensing UV spectrum light and IR spectrum light, outputting a first output signal when the IR signal is above an IR threshold and the UV signal is below a UV threshold, and generating an alert based on the first output signal. Some variations may optionally comprise displaying an instruction to apply sunscreen over the target skin region or acquiring an image that includes the target skin region and displaying a composite image that comprises a graphic of the sensor field overlaid over the image. The sensor system may comprise an optic to limit the sensor field. The optic may be, for example, a fiber-optic faceplate, or a diffraction optic, or a low numerical-aperture hole array. The sensor field may have an effective field of view in the range of 5 degrees to 180 degrees, or 15 degrees to 135 degrees, or 30 degrees to 90 degrees, for example. In other embodiments, the sensor field may be characterized as an area in the range of 0.1 to 1500 $cm^2$ at a distance of 5 cm from the sensor system, and in some variations, the sensor field may have an area in the range of 0.5 to 20 $cm^2$ at a distance of 5 cm, or 1 to 15 $cm^2$ at a distance of 5 cm from the sensor system. In some variations, the sunscreen detector may comprise a sensor module, and the illumination system and the sensor system may be located on the sensor module. The sensor module may be located in a cell phone, or a watch, or in a band of a watch. The controller may be configured to overlay a graphic corresponding to the sensor field onto a camera image. For example, the graphic may be a first graphic corresponding to the first output signal. The controller may be further configured to output a second output signal when the IR signal is above an IR threshold and the UV signal is above a UV threshold, and the graphic may be a second graphic corresponding to the second output signal. The controller may also be configured to output a third output signal when the IR signal is below an IR threshold, and the graphic may be a third graphic corresponding to the third output signal. Optionally, the illumination system may be further configured to emit visible light.

In some variations, a method for detecting sunscreen coverage may optionally comprise calibrating a UV-IR spectrometer that may be a sunscreen detector. Calibrating the sunscreen detector may comprise scanning a skin region that has no sunscreen to acquire a baseline skin UV spectrum light measurement and a baseline skin IR spectrum light measurement. In further variations, calibrating the sunscreen detector may comprise placing the sunscreen detector against a skin region that has no sunscreen, acquiring a first measurement comprising a UV spectrum light level and an IR spectrum light level, pulling the sunscreen detector away from the skin region, acquiring a plurality of measurements while pulling the sunscreen detector away from the skin region, each of the measurements comprising a UV spectrum light level, an IR spectrum light level, and a distance between the detector and the skin region, and calculating, using the controller, the UV threshold and IR threshold based on the plurality of measurements. The sunscreen detector may be pulled away from the skin surface to a separation distance in the range of about 1 in to about 18 in, or about 3 in to about 10 in, or about 3 in to about 7 in. In some variations, the controller may be configured to determine melanin levels in the skin region based on the plurality of measurements. Calculating the UV threshold and IR threshold may comprise calculating the ratio of UV spectrum light level of each of the plurality of measurements to the UV spectrum light level of the first measurement. Optionally, a calibration method may comprise using the controller to generate a calibration curve based on the first measurement and the plurality of measurements.

BRIEF DESCRIPTION OF THE DRAWINGS

FIG. 2B depicts another variation of a UV-IR spectrometer.

FIG. 3A is a perspective view and cross-sectional view of one variation of an optic of a UV-IR spectrometer.

FIG. 3B is a cross-sectional view of another variation of an optic of a UV-IR spectrometer.

DETAILED DESCRIPTION

Described herein is a device that detects the UV light that may be reflected by a user-selected region. The UV-IR spectrometers described herein may be sunscreen detectors and incorporated in mobile and/or wearable devices. The UV-IR spectrometer may be used to scan the user's skin and based on the detected UV light values (which may be UV reflectance values), determine whether the user should apply sunscreen, and/or should apply additional sunscreen, and/or whether the scanned skin region is at risk for UV light exposure. The UV-IR spectrometer may comprise an illumination system having a UV light source, a sensor system having a UV sensor, and a controller in communication with the illumination and sensor systems. Optionally, the illumination system may also have an infrared (IR) light source, and the sensor system may have an IR sensor. The illumination and sensor systems may be located on a wearable or mobile device, while the controller may be located on a separate device, for example, a computer or a separate wearable or mobile device. Alternatively, the illumination system, sensor system and controller may all be located on the same wearable or mobile device. For example, the UV-IR spectrometer may be located on a wrist-worn device (e.g., a watch, wrist-band, or bracelet), an article of clothing (e.g., hat, glasses), or a smart phone or tablet. In some variations, the illumination and sensor systems may be located on the wrist-worn device, an article or clothing or a smart phone, while the controller may be located on a tablet, laptop, or desktop computer. In some variations, the UV-IR spectrometer may be integrated with these other devices, but in other variations, the UV-IR spectrometer may be in a separate module that is attachable by a user to a wearable or mobile device. For example, the UV-IR spectrometer may comprise an adaptor configured to attach to a port (e.g., a USB port) of a computing device. In some variations, the UV-IR spectrometer may have a dedicated controller distinct from the controller of the wearable or mobile device and the controller of other computing devices (e.g., tablet, laptop, desktop computer, remote server, etc.). The spectrometer controller may perform spectrometer-specific methods and/or may perform general computing methods. Any of the methods described below may be performed by the spectrometer controller, the wearable or mobile device controller, the computing device controller, and/or a combination of two or more of these controllers. For example, methods for IR depth mapping may be performed by the spectrometer controller while methods for generating user notifications may be performed by the wearable or mobile device controller. Analysis and interpretation of scan data, calibration data, including light level threshold computation, IR depth mapping, user notification methods, and storage of data of any kind may be performed by one or more of the controllers described above.

Figure 1A:
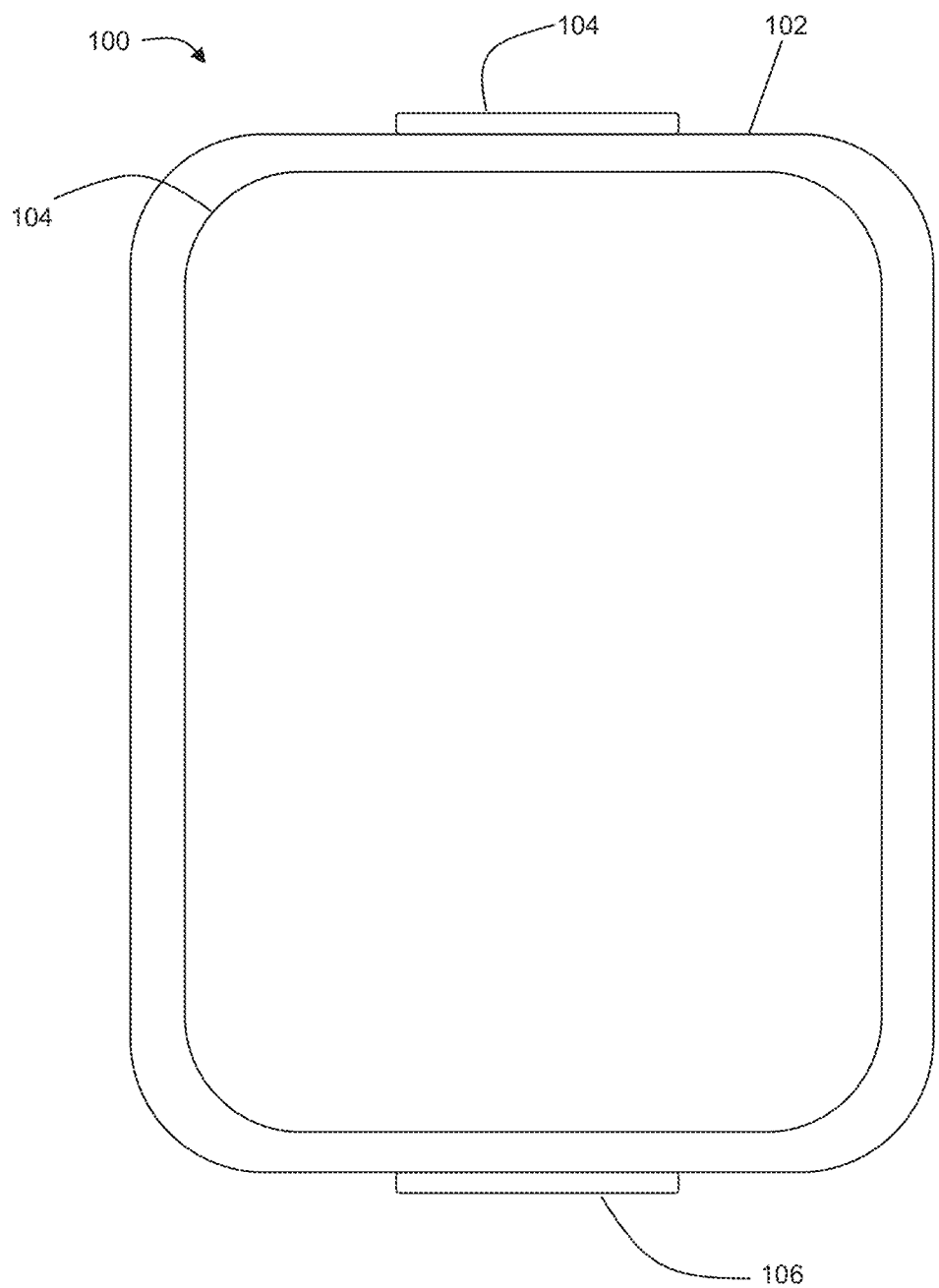
FIG. 1A illustrates a personal electronic device in accordance with some variations.
Figure 1B:
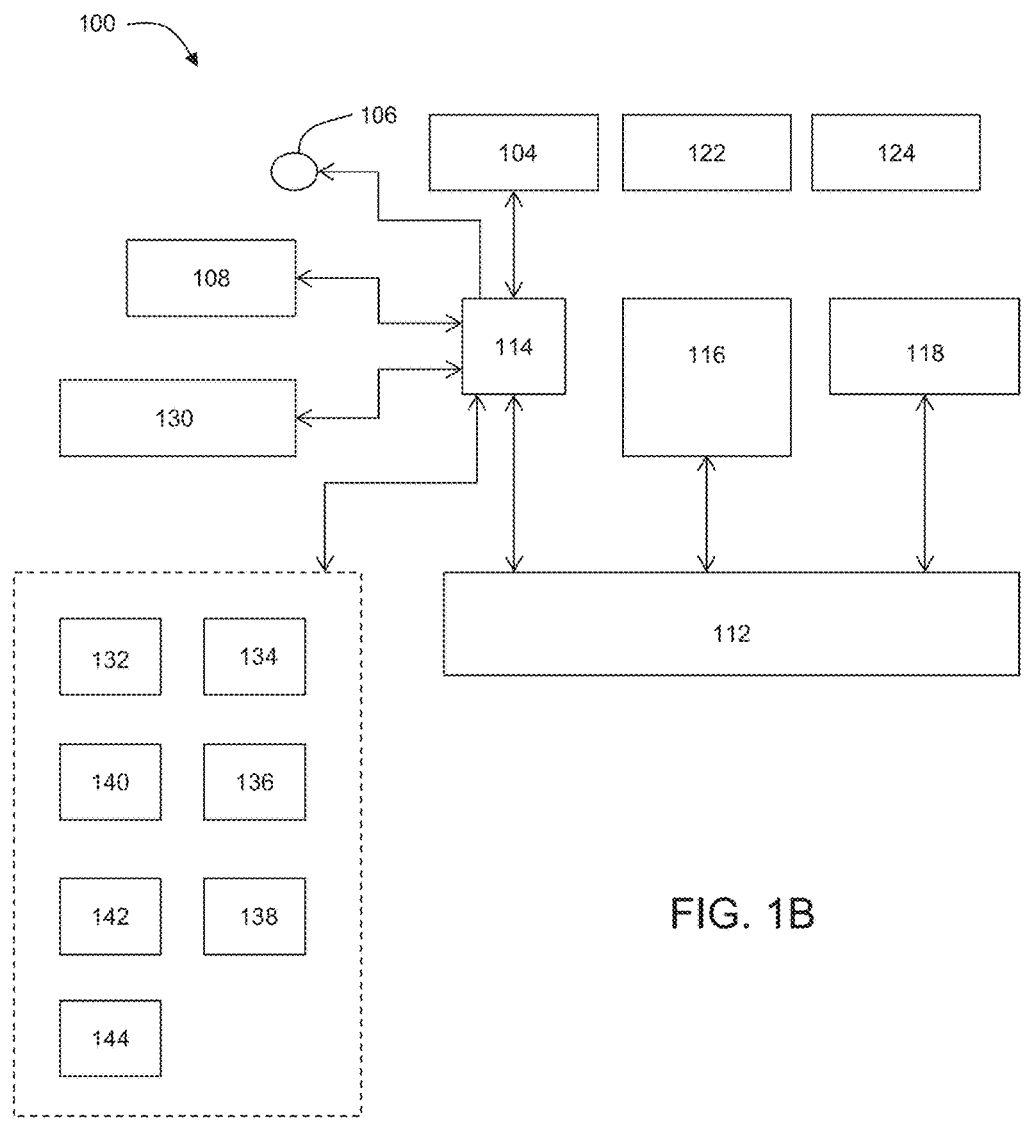
FIG. 1B is a block diagram illustrating a personal electronic device in accordance with some variations.

FIGS. 1A-1B provide a description of exemplary devices for performing the techniques for operation and use of a UV-IR spectrometer.

Although the following description uses terms "first," "second," etc. to describe various elements, these elements should not be limited by the terms. These terms are only used to distinguish one element from another. For example, a first light source could be termed a second light source, and, similarly, a second light source could be termed a first light source, without departing from the scope of the various described variations. The first light source and the second light source are both light sources, but they are not the same light source.

The terminology used in the description of the various described variations herein is for the purpose of describing particular variations only and is not intended to be limiting. As used in the description of the various described variations and the appended claims, the singular forms "a", "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Variations of electronic devices, user interfaces for such devices, and associated processes for using such devices are described. In some variations, the device is a portable communications device, such as a mobile telephone, an internet-enabled telephone such as a smartphone, or a wearable communications device, such as a wristband, watch, clip, headband, earphone or ear piece, internet-enabled eyewear, or any computing device, portable or otherwise, such as a personal calendaring device, electronic reader, tablet, desktop, or laptop computers, etc. Any of these devices may also contain other functions, such as personal digital assistant (PDA) and/or music player functions. Optionally, any of the above-listed electronic devices may comprise touch-sensitive surfaces (e.g., touch screen displays and/or touchpads). Alternatively or additionally, the electronic devices may include one or more other physical user-interface devices, such as a physical keyboard, a mouse, and/or a joystick.

FIG. 1A illustrates exemplary personal electronic device 100. Device 100 includes body 102. Personal electronic device 100 may be a portable device such as a smart phone, tablet, watch, and in some variations, may be part of a wireless-capable eyepiece or eyewear, headgear, and the like. In other variations, personal electronic device 100 may not be a portable device, and may be desktop computer. In some variations, device 100 has touch-sensitive display screen 104. Alternatively, or in addition to touch screen 104, device 100 may have a display and a touch-sensitive surface. In some variations, touch screen 104 (or the touch-sensitive surface) may have one or more intensity sensors for detecting intensity of contacts (e.g., touches) being applied. The one or more intensity sensors of touch screen 104 may provide output data that represents the intensity of touches. The user interface of device 100 can respond to touches based on their intensity. For example, touches of different intensities can invoke different user interface operations on device 100.

In some variations, device 100 may have one or more input mechanisms 106 and 108. Input mechanisms 106 and 108, if included, can be physical. Examples of physical input mechanisms may include push buttons and rotatable mechanisms. In some variations, device 100 may have one or more attachment mechanisms. Such attachment mechanisms, if included, can permit attachment of device 100 with, for example, hats, eyewear, earrings, necklaces, shirts, jackets, pockets, collars, bracelets, watch straps, chains, trousers, belts, shoes, socks, purses, backpacks, undergarments, and so forth. These attachment mechanisms may permit device 100 to be worn by a user.

FIG. 1B depicts exemplary personal electronic device 100. Device 100 has bus 112 that operatively couples I/O section 114 with one or more computer processors 116 and memory 118. I/O section 114 may be connected to display 104, which may have a touch-sensitive component 122 and, optionally, a touch-intensity sensitive component 124. In addition, I/O section 114 may be connected with communication unit 130 for receiving application and operating system data, using Wi-Fi, Bluetooth, near field communication (NFC), cellular, and/or other wireless communication techniques. Device 100 may include input mechanisms 106 and/or 108. Input mechanism 106 may be a rotatable input device or a depressible and rotatable input device, for example. In some examples, input mechanism 108 may be a button.

Input mechanism 108 may be a microphone, in some examples. Personal electronic device 100 can include various sensors, such as GPS sensor 132, accelerometer 134, directional sensor 140 (e.g., compass), gyroscope 136, motion sensor 138, and/or a combination thereof, all of which can be operatively connected to I/O section 114. Embodiments with a UV-IR spectrometer, described in greater detail below, may include an UV sensor 142 and/or an IR sensor 144.

Memory 118 of personal electronic device 100 can be a non-transitory computer-readable storage medium, for storing computer-executable instructions, which, when executed by one or more computer processors 116, for example, can cause the computer processors to perform the techniques described herein. The computer-executable instructions can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. A "non-transitory computer-readable storage medium" can be any medium that can tangibly contain or store computer-executable instructions for use by or in connection with the instruction execution system, apparatus, or device. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 100 is not limited to the components and configuration of FIG. 1B, but can include other or additional components in multiple configurations.

Attention is now directed towards variations of additional device modules and associated processes that may be implemented on an electronic device, such as device 100.

Figure 2A:
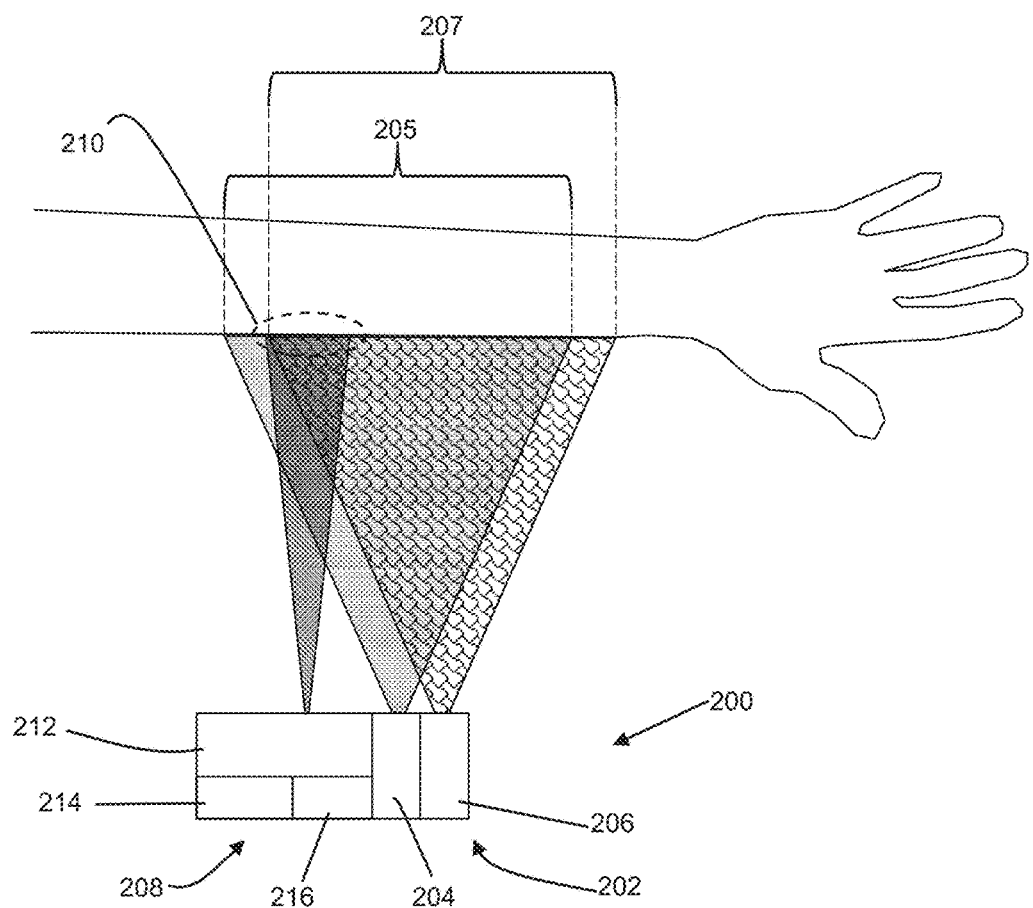
FIG. 2A depicts one variation of a UV-IR spectrometer.

A UV-IR spectrometer may be a sunscreen detector configured to determine whether a user should apply sunscreen based on detected UV light measurements. In some variations, a UV-IR spectrometer may be configured to detect IR light measurements, and may optionally use the IR light measurements in conjunction with the UV light measurements to determine whether a user should apply sunscreen. The UV-IR spectrometer may generate an alert and/or message to the user with its sunscreen recommendation, which may include whether sunscreen is to be applied, and optionally, the amount and strength (e.g., SPF) of the sunscreen. The sunscreen detector may also prompt the user to apply sunscreen to a particular location. One variation of a UV-IR spectrometer or sunscreen detector 200 is depicted in FIG. 2A. As depicted there, the illumination system 202 of the UV light or sunscreen detector 200 may comprise a UV LED 204 with a first illumination field 205 and an infrared (IR) LED 206 with a second illumination field 207 that at least partially overlaps with the first illumination field 205 of the UV LED. The UV and IR light reflected by the skin located within the first and second illumination fields are detected by a sensor system 208. The field of view (FOV) 210 of the sensor system overlaps with at least a portion of the illumination fields of the illumination system. In some variations, the FOV 210 of the sensor system may at least partially overlap with the illumination fields 205, 207 of the illumination system 202, for example, may overlap with the illumination fields 205, 207 of both the UV LED and IR LED. Optionally, the FOV 210 of the sensor system may be smaller than the illumination fields 205, 207 of the illumination system. For example, the FOV of the sensor system may be about 5% to about 70% of the illumination fields, e.g., about 10%, about 25%, about 35%, about 40% etc. The size and shape of the FOV 210 may be determined at least in part by an optic 212. The optic 212 may comprise a fiber-optic faceplate, a low numerical-aperture array, a microlens array, or any structure that modifies the direction of light that is incident on the UV and/or LED sensors (e.g., optic may focus or scatter light, or may transmit light of a particular polarity or direction). The sensor system 208 may detect the amount of UV and IR light reflected by the skin, and the controller may infer the amount of UV and IR light absorbed by the sunscreen or skin. In some variations, the sensor system 208 may comprise a UV light sensor 214 and an IR light sensor 216, while in other variations, the sensor system may comprise a single light sensor that is capable of sensing both UV and IR light. The amount of UV and IR light detected by the sensor(s) may be communicated to the controller, which may then compare those measured values with predetermined UV and IR thresholds, respectively. Based on the values of the reflected UV and IR light with respect to those thresholds, the controller notifies the user as to whether the skin located within the FOV of the sensor system is at risk of UV exposure, and/or whether sunscreen needs to be applied to that skin region.

In addition to receiving data from the sensor system, the controller may issue commands to the illumination and sensor systems. For example, the controller may issue a series of commands to the illumination system and the sensor system as part of a calibration procedure. The calibration procedure may be automatically initiated upon powering on the UV-IR spectrometer, or user-initiated as desired. The controller may also notify the user if the UV-IR spectrometer is improperly used. For example, the controller may notify the user if the movement of the UV-IR spectrometer across the region of interest is not continuous, irregular (e.g., the distance between the spectrometer and the skin surface is not substantially constant during the scan), too fast, etc. The controller may also be configured to store user identification data, as well as time-based UV and IR data associated with that user. Based on the stored data, a computer-implemented method on the controller may be executed to remind the user of the time of the last sunscreen application and prompt the user to reapply sunscreen before the sun protection ability of the previously applied sunscreen is depleted. A computer-implemented method in the controller may also be configured to recognize when the user is in an elevated UV environment (e.g., outdoors) based on the detected UV sensor data and prompt the user to apply sunscreen to exposed skin regions. Optionally, the controller may have a computer-implemented method that includes steps to map UV and IR data onto image data to form a composite image. Areas with high UV reflectance may be annotated in the image by an outline or pseudo-coloring or shading. For example, UV and IR data may be mapped onto the image of a child, and areas where the UV reflectance is high (i.e., where sunscreen may need to be applied and/or skin regions having an elevated risk of UV exposure) may be outlined and/or shaded and/or colored.

Illumination System

In one variation of a UV-IR spectrometer or sunscreen detector, the illumination system may comprise an UV light source and an IR light source. The UV light source may be a LED that emits light having a peak wavelength or otherwise sufficient intensity in the range of about 290 nm to about 320 nm (e.g., in the UVB range). Applying a specific wavelength of UV light may also help the UV-IR spectrometer to provide an absolute measurement of the amount of UV light that is reflected or absorbed by the target skin surface. Optionally, a UV-IR spectrometer may comprise a UV light source that emits light at two wavelength bands. For example, a UV light source may comprise a first LED that is configured to emit light in the UVB range (e.g., from about 290 nm to about 320 nm) and a second LED that is configured to emit light in the UVA range (e.g., from about 320 nm to about 400 nm). A UV light source capable of emitting light in the UVA and UVA bands separately may allow a user to determine the efficacy of a particular sunblock under different UV light conditions. For example, a user may be able to determine if a particular sunblock and/or level of sunblock coverage blocks UVA light better than it blocks UVB light (or vice versa), or if such sunblock and/or coverage level blocks both bands of UV light approximately equally. The IR light source may be a LED that emits light having a peak wavelength or otherwise sufficient intensity in the range of about 850 nm to about 950 nm. Illumination with IR may help the UV-IR spectrometer to track the presence and/or location of a body part in the field of view. The reflectance of IR light from the target skin helps the sunscreen detector to identify the difference between a well-protected body region in a field of view and no body part in the scanning field (since both scenarios would present with low UV reflectance). A well-protected body region may include a body region that is covered by clothing (e.g., shirt sleeves, scarves, towels, robes, and the like), and/or adequately covered by sunscreen, and in some variations, IR illumination and detection may be used to distinguish between UV protection provided by textiles (e.g., clothing) and sunscreen lotion. The intensity of the UV and IR light sources may be in the range of about 0.001 W/cm$^2$ to about 0.5 W/cm$^2$, about 0.02 W/cm$^2$ to about 0.2 W/cm$^2$, or about 0.2 W/cm$^2$ to about 0.3 W/cm$^2$ for example, at a distance of 5 cm from the sensor system. The intensity of the UV and/or IR sources may be selected to provide a baseline reflectance level in a variety of natural or artificial ambient light conditions, while also generating minimal, if any, risk of skin damage or irritation from one or more of the light sources. In some variations, the UV light source may be pulsed so that UV light exposure risks to the user are reduced or mitigated. For example, the UV light source may be pulsed at duty cycle where the light pulse activated long enough for a measurement to be procured, but is deactivated for the rest of the cycle. For example, the UV light source may be pulsed at a frequency from about 1 Hz to about 1 kHz (e.g., from about 1 Hz to about 10 Hz, from about 10 Hz to about 25 Hz, from about 24 Hz to about 75 Hz, from about 74 Hz to about 100 Hz, from about 100 Hz to about 120 Hz, from about 115 Hz to about 200 Hz, from about 190 Hz to about 400 Hz, from about 350 Hz to about 600 Hz, from about 580 Hz to about 800 Hz, from about 799 Hz to about 1 kHz, etc.) with a duty cycle from about 1% to about 99% (e.g., from about 1% to about 30%, from about 29% to about 50%, from about 49% to about 75%, from about 70% to about 90%, from about 85% to about 99%, from about 1% to about 10%, from about 24% to about 50%, from about 45% to about 70%, from about 60% to about 80%, etc.). The illumination field of the UV light source and the IR light source may be similar or the same, and at least a portion of the illumination fields of the UV and IR light sources overlap. The illumination fields of the UV and IR light sources may be circular, rectangular, or any desired shape, and may have an illumination area from about 0.1 cm$^2$ to about 1500 cm$^2$ when the UV-IR spectrometer is located about 5 cm from the skin. The area of the overlap between the illumination field of the UV light source and the IR light source may from about 0.1 cm$^2$ to about 1500 cm$^2$ when the UV-IR spectrometer is located about 5 cm from the skin, or from about 0.5 cm$^2$ to about 20 cm$^2$ when the UV-IR spectrometer is located about 5 cm from the skin, or from about 1 cm$^2$ to about 15 cm$^2$ when the UV-IR spectrometer is located about 5 cm from the skin.

Optionally, an illumination system may comprise a visible light source that is configured to outline or otherwise indicate to the user the region of the UV and IR illumination fields that overlap. One variation of a UV-IR spectrometer or sunscreen detector 220 with an illumination system 222 comprising a visible light source 223 is depicted in FIG. 2B. The illumination system 222 may comprise a UV LED 224 having an illumination field 225, an IR LED 226 having an illumination field 227, and a visible light LED 223 having an illumination field that is enclosed within the region 230. The visible light LED 223 may emit any wavelength light that is visible to the human eye, for example, light with a wavelength between about 390 nm to about 700 nm. The illumination field of the visible light LED 223 may at least overlap with, or is the same or similar to, the FOV of the sensor system 228, which is denoted in the region 230 enclosed in the dotted lines. The illumination field of the visible light LED 223 may have a circular or other shape when projected onto a region of skin that at least partially overlaps with the FOV of the sensor system. Alternatively or additionally, the illumination field of the visible light LED 223 may be substantially smaller than the FOV of the sensor system 228. For example, the visible light LED may emit a beam of light that projects as a point on a skin region. The point may indicate the center of the FOV of the sensor system, without indicating the boundaries of the FOV. Providing a visible light source to indicate the general location and/or size of the sensor system FOV may help to guide the user as they scan the skin surface so that they can move the UV-IR spectrometer in a continuous (e.g., continuous speed) and constant fashion, and keep the spectrometer pointed at the target skin region. The visible light source may have an illumination field that corresponds to the overlap region, and if the size of the visible light illumination field changes during the scan, the user would know that they were not keeping the distance between the UV-IR spectrometer and the skin substantially constant (e.g., if the illumination field of the visible light appeared bigger as they scanned across, the user would know that they were moving the spectrometer further from the skin as they scanned), which would offer the user the opportunity to adjust their scan motion. Similarly, if the illumination field of the visible light was moved off the skin (e.g., when not scanning straight across an arm or leg) the user would also know that they needed to adjust their scan motion to keep the UV-IR spectrometer within the boundaries of the skin region.

The UV, IR and visible light sources described above may be pulsed or may provide a continuous illumination during the scan period. For example, the UV and IR light sources may be alternately pulsed (e.g., when the UV light source is activated, the IR light source is not activated and vice versa, pulsed out-of-phase), and/or they may be simultaneously pulsed (e.g., pulsed in-phase). The optional visible light source may be continuously activated or pulsed in-phase or out-of-phase with the UV and/or IR light sources.

Sensor/Measurement System

One variation of a sensor system may comprise an optic and one or more light sensors configured to detect UV and IR light. The amount of UV and IR light detected by the sensor module may be used to determine whether any sunscreen has been applied to the target skin region, and if any sunscreen has been applied, whether the sunscreen coverage and quantity is sufficient for safe sun exposure. The detected UV and IR light levels may also be used to determine whether the scanned skin region is at risk for UV exposure. The detected UV light indicates how much UV light has been reflected from the target skin region and the detected IR light may confirm the presence of the target skin region, and may also be used to determine how far the UV-IR spectrometer is from the skin. For example, the IR channel may provide data to the controller to compute the proximity of the spectrometer to the target skin region, and optionally, the controller may alert the user as to whether the target skin region is in the range of the UV-IR spectrometer. In some variations, a sensor system may comprise a single light sensor that has one or more filters (e.g., mosaic filters and the like) disposed over the light-sensitive portion of the sensor, which may allow the sensor to simultaneously detect different wavelength light (e.g., UV and IR light, UV, IR and visible light, IR and visible light, UV and visible light, etc.). In other variations, a sensor system may comprise a first UV light sensor, a second IR light sensor, and an optional third visible light sensor. Using multiple, separate LEDs and detectors for IR and UV light may help increase the accuracy of the UV-IR spectrometer, since it may help reduce the cross-talk between the IR and UV channels. A sensor system with relatively fewer components (such as the examples described herein) may have a substantially smaller form factor and may consume less power than a sensor system with more components, and accordingly may be suitable for integration into mobile devices and/or wearable devices.

One example of a sensor module 208 is depicted in FIG. 2A. Sensor module may comprise an UV sensor, an IR sensor, and a FOV-reducing optic. The UV sensor and the IR sensor are configured to measure the amount of UV and IR light from the illumination module that is reflected off the target skin region. The amount of UV light reflected from the skin may be an indication of the amount of sunscreen applied and/or whether the user should apply more sunscreen.

The optic of a sensor system may be configured to define the field-of-view (FOV) of the sensor system, and may have a lens-based or lens-less design. In some variations, the optic may reduce the FOV such that it is smaller than the illumination fields of the UV and IR light sources. The FOV of the sensor system may also be smaller than the area of the overlap between the UV and IR illumination fields. For example, the sensor system FOV may have an area from about from about 0.1 cm$^2$ to about 1500 cm$^2$ when the UV-IR spectrometer is located about 5 cm from the skin, or from about 0.5 cm$^2$ to about 20 cm$^2$ when the UV-IR spectrometer is located about 5 cm from the skin, or from about 1 cm$^2$ to about 15 cm$^2$ when the UV-IR spectrometer is located about 5 cm from the skin. As with the illumination fields of the illumination system, the FOV of the sensor system may have any shape, such as circular, rectangular, or any desired shape. The FOV of the sensor system may include at least a portion of the overlap region between the UV illumination field and the IR illumination field, and in some variations, may substantially encompass the entire overlap region, for example, the FOV may be coincident with at least about 20%, 30%, 40%, 50%, 60%, 70%, 80%, 90% or 100% of the overlap region between the UV illumination field and the IR illumination field. In some variations, the effective FOV of the sensor system may be from about 5 degrees to about 180 degrees, or from about 15 degrees to about 135 degrees, or from about 30 degrees to about 90 degrees. In some variations, the FOV of the sensor system may be coincident with the overlap region, but smaller than the overlap region. Optionally, the FOV of the sensor system may have a similar size and shape to the illumination field of the visible light source. Field-reducing optics may include a fiber-optic faceplate 302 as depicted in FIG. 3A, a narrow or low numerical aperture array 304 as depicted in FIG. 3B, a collimated microlens array, a fiber-optic array plate, and the like. The optic may be less than about 1 mm thick. The geometry of the optic may be such that the light gathered by the optic and directed to the sensor is from a narrowly selected FOV. Narrowing the FOV of the sensor system to a small patch or spot may help to limit ambient cross-talk, such that the dominant UV and IR signals are from the target skin region, and may allow a user to specifically select a patch or an area-constrained or an area-restricted region of skin to be analyzed. Additionally or alternatively, the optic may be adjusted to alter the FOV and/or the amount of light that is detected by the sensor system. For example, an optic may comprise an adjustable aperture, where the diameter of the aperture may be changed by the user in order to alter the amount and direction of light that is captured by the light sensors. In other variations, the distance between the sensor and the optic may be adjusted to vary the FOV, using a motor or microelectromechanical system, for example, or an electronically adjustable liquid lens. Varying the distance between the sensor system and the skin region to be analyzed may alter the field from which light is collected by the optic. While in some variations, the optic is described as narrowing the FOV, in other variations, the optic may configured to view multiple portions of a body part at once, thereby increasing the overall scan speed. For example, the optic may have multiple angles that may form multiple distinct FOVs at different skin regions, which may allow the UV and IR sensors to detect the UV and IR reflectance of multiple portions of a body part at one time. In some variations, a sensor system may have a single optic with multiple angles, or multiple optics each with different angles. Functionally, this may provide for multiple FOVs that allow for the scanning of multiple skin regions (e.g., multi-point scanning). For example, a system may have a first optic with a first angle in a first direction and a second optic with a second angle in a second direction. The first optic may have a first FOV and the second optic may have a second FOV, where the first FOV may include skin at a first region and the second FOV may include skin at a second region. The first optic may direct light to a first region of the light sensor and the second optic may direct light to a second region of the light sensor so that each FOV may be monitored separated. Alternatively, instead of directing light to different regions of a single light sensor, the first and second optics may direct light to two distinct light sensors. Scanning multiple regions simultaneously may allow for a faster scan of the entire body part.

As briefly described above, the amount of IR light reflected from the skin may be used to compute the proximity of the UV-IR spectrometer to the target skin. For example, based on the amount of IR light detected by the sensor system, the controller may be configured to calculate the distance between the UV-IR spectrometer and the target skin, and if the distance is outside of a pre-determined working range of the sensor system, the controller may generate a pointing error alert and notify the user to adjust the position of the spectrometer. In some variations, the controller may use IR depth mapping methods to calculate the distance between the spectrometer and the target skin. For example, if the amount of IR light falls below a first pre-determined threshold and/or the controller calculation indicates that the distance is too far, the controller may alert the user to improper scanning due to the target skin region not being located within the FOV of the UV-IR spectrometer, or the user holding the UV-IR spectrometer too far from the target skin region. If the amount of IR light is above a second pre-determined threshold and/or the controller calculation indicates that the distance is too close, the controller may alert the user to improper scanning due to the user holding the spectrometer too close to the target skin region. The controller may also calculate the change in the distance over time (e.g., over the duration of the scan), and if the distance fluctuates beyond a certain threshold, the controller may also generate an alert to the user. These cues may help a user to position the UV-IR spectrometer such that the distance from the spectrometer to the target skin region is within the working range of the spectrometer, and/or to help the user position the spectrometer at a relatively consistent and/or constant distance away from the skin region during the scan.

Controller

The UV and IR light data collected by the sensor system may be communicated to the controller, which has one or more computer-implemented methods that interpret the data and provides instructions to the user based on the analyzed data. The controller may also have one or more calibration protocols, which will be described below. One example of a computer-implemented method that may be stored and executed in the non-transitory computer-readable media of a controller is functionally represented in Table 1 and depicted in FIG. 4. The measured UV and IR values are compared against a UV threshold and an IR threshold, respectively. The UV and IR thresholds may be predetermined before the scan. For example, these thresholds may be determined at least in part by user-input data (e.g., age, gender, preferred UV light protection and/or risk tolerance, etc.), and/or a calibration protocol (e.g., which may determine baseline levels of melanin in a user's skin, ambient light levels, etc. before and/or after the application of sunblock). In some variations, the UV and IR thresholds may be determined by a method comprising performing a calibration scan before the application of sunblock to define an upper threshold limit, performing a calibration scan after the application of sunblock to define a lower threshold limit, and selecting a value between the upper threshold limit and lower threshold limit. Examples of various calibration protocols are described further below. The UV light data from the UV sensor may be compared with the UV threshold and the IR light data from the IR sensor may be compared with the IR threshold. Depending on the results of these comparisons, the controller may provide certain indications and instructions to the user. Examples of such indications and instructions are outlined in Table 1. An annotation of "low" indicates that the measured light level is below the threshold and an annotation of "high" indicates that the measured light level is at or above the threshold.

TABLE 1

| | Measured IR level | Measured UV level | Interpretation | Message to the user |
|---|---|---|---|---|
| 1 | Low | Low or High | No body part in scan region or insufficient measurement | Error indicator (e.g., blinking red light); prompt user to point the detector to a target region with a body part |
| 2 | High | Low | Scanned body part has sufficient sunscreen protection | Positive reinforcement (e.g., blinking green light) |
| 3 | High | High | Scanned body part has insufficient sunscreen protection | Warning indicator (e.g., blinking yellow light); prompt user to apply sunscreen to scanned region |

Figure 4:
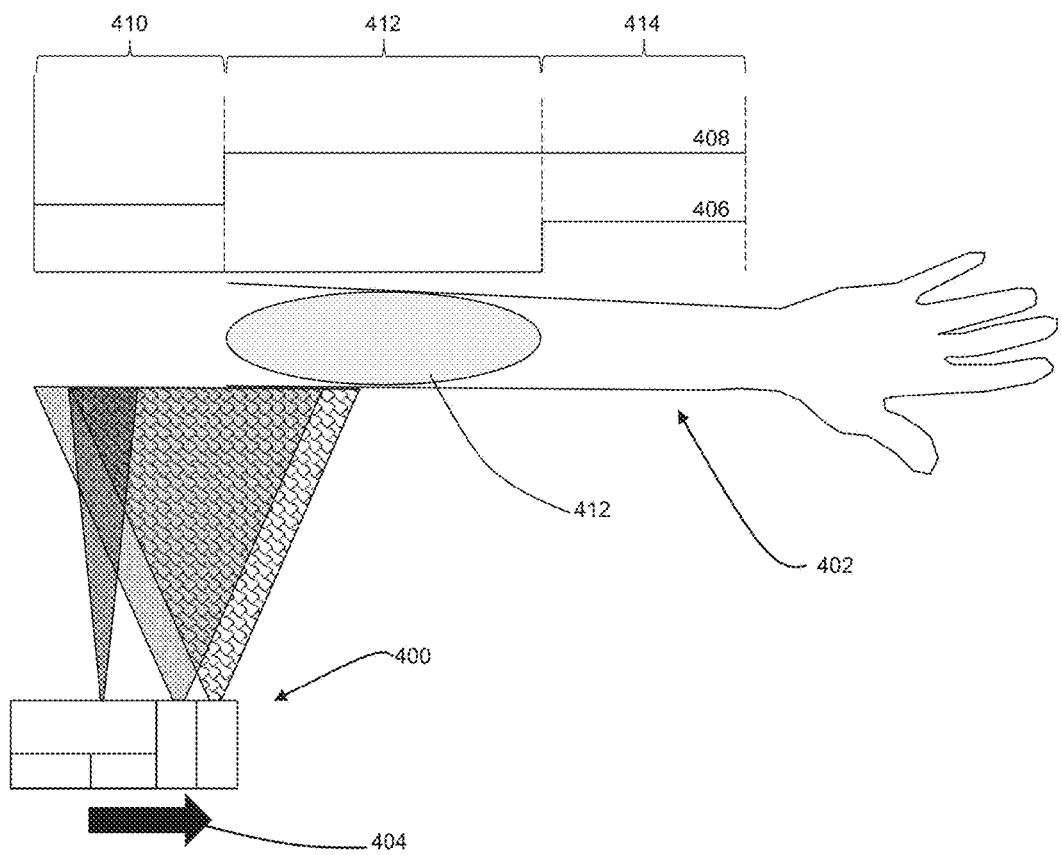
FIG. 4 conceptually depicts the output of a sensor system of a UV-IR spectrometer as scans a target tissue region.

FIG. 4 depicts an example of a UV-IR spectrometer or sunscreen detector 400 that is being scanned over the target body region 402 in the direction indicated by the arrow 404. As the UV-IR spectrometer 400 is moved over the body region (e.g., arm) 402, the measured UV and IR light levels may vary as depicted in the waveforms 406 and 408, respectively. The measured light levels may be used to look up the appropriate interpretation and user message in a matrix (of which Table 1 is an example). At the beginning of the scan, the UV-IR spectrometer 400 may be located over a region 410 with no body part, so the measured UV light level 406 and IR light level 408 may be low. If the UV-IR spectrometer 400 is located over a skin region 412 that is adequately protected by sunscreen, the measured IR light level 408 may be high (indicating the presence of a body region) and the measured UV light level 406 may be low (indicating that the UV light was largely absorbed by the sunscreen). If the UV-IR spectrometer 400 is located over a skin region 414 that is not adequately protected by sunscreen (or has no sunscreen at all), the measured IR light level 408 may be high (indicating the presence of a body region) and the measured UV light levels 406 may be high (indicating that the UV light was not absorbed by the sunscreen or skin). In addition to comparing a measured light level to a predetermined threshold, the controller may also be programmed to store the actual measured values of the UV and IR light. For example, the raw measured values from the IR channel may be used to compensate for changes in the measured UV light levels in the UV channel due to distance variations. If the distance from the UV-IR spectrometer to the target skin region changes, the amplitude of the measured IR and UV light will also change. The amplitude of the IR channel data may be used to normalize the amplitude of the UV channel data, which may help to mitigate sensor motion artifacts due to distance variation. In addition to storing data acquired by the light sensors, the controller memory may also store time data of various events (e.g., time of last scan, time of last calibration), user identification data (e.g., name, gender, age, skin profile/characteristics), location data (e.g., GPS coordinates), images, previously computed UV and IR thresholds, etc. The controller memory may also contain cross-references and indexes to such data. For example, the controller memory may link the time data associated with light sensor data, location data, etc. to a particular user skin profile (e.g., baseline reflectance values, melanin content, etc.) so that when that user scans their skin, the UV-IR spectrometer recognizes that user's skin, and uses previously computed UV and IR thresholds and other custom settings when interpreting that user's scan data. Time data may be used by the controller to generate reminders or alarms to the user as to when to re-apply sunscreen, and/or to limit sun exposure. These reminders may be tailored to each individual user based on the time of their last sunscreen application and how much sunscreen coverage was provided at that application. For example, if a heavy layer of sunscreen was initially applied, the reminder to re-apply may occur at a later time than if a lighter layer of sunscreen was initially applied.

Optionally, the controller may have a plurality of UV and/or IR light thresholds, and may provide a different set of notifications and indications based on each of the thresholds. For example, a controller may have a computer-implemented method stored in non-transitory computer-readable media that has two or more UV light thresholds or levels, where each UV light threshold represents a different degree of UV light protection or risk level. As previously described, these UV light thresholds may be determined by user-input and/or computed by the controller based on data collected during a calibration protocol. In some variations, the controller may recommend applying sunscreen lotions of varying SPF values based on whether the measured UV light levels exceed certain of these UV light thresholds. For example, a computer-implemented method may three UV light thresholds: low, medium and high. If a measured UV light level is at or above the high threshold, the controller may generate a notification to the user that recommends the use of sunscreen lotion having an SPF value of 45 or more. If a measured UV light level is at or above the medium threshold but below the high threshold, the controller may generate a notification to the user that recommends the use of sunscreen lotion having an SPF value of 30 or more. If a measured UV light level is at or above the low threshold but below the medium threshold, the controller may generate a notification to the user that recommends the use of sunscreen lotion having an SPF value of 15 or more. Optionally, a computer-implemented method may also include steps that include a plurality of IR light thresholds.

The controller of a UV-IR spectrometer or sunscreen detector may be programmed with a calibration sequence or protocol that may be automatically initiated when the detector is powered on, or may be initiated as desired by a user. For example, the calibration sequence may be initiated based on user command when the user moves from an indoor space to an outdoor space (or any circumstance that results in changes in ambient light levels), and/or when the detector is used to scan different users, and/or when different body parts are to be scanned. Calibrating the UV-IR spectrometer under these circumstances may help the controller to account for the different reflective properties of different parts of the body, skin variability affecting UV absorption (e.g., pigment/melanin content, moisture content, sweat content, etc.). A calibration sequence may comprise steps to be completed by the user (e.g., a manual calibration protocol where some or all of the steps require user participation) and/or may comprise steps executed by the UV-IR spectrometer (e.g., a self-calibrating calibration protocol where some or all of the steps are executed by the controller). Alternatively, a calibration protocol may not require the user to take any steps beyond initiating the calibration protocol. Examples of calibration protocols that comprise user executed and/or controller executed steps are described below.

Figure 5:
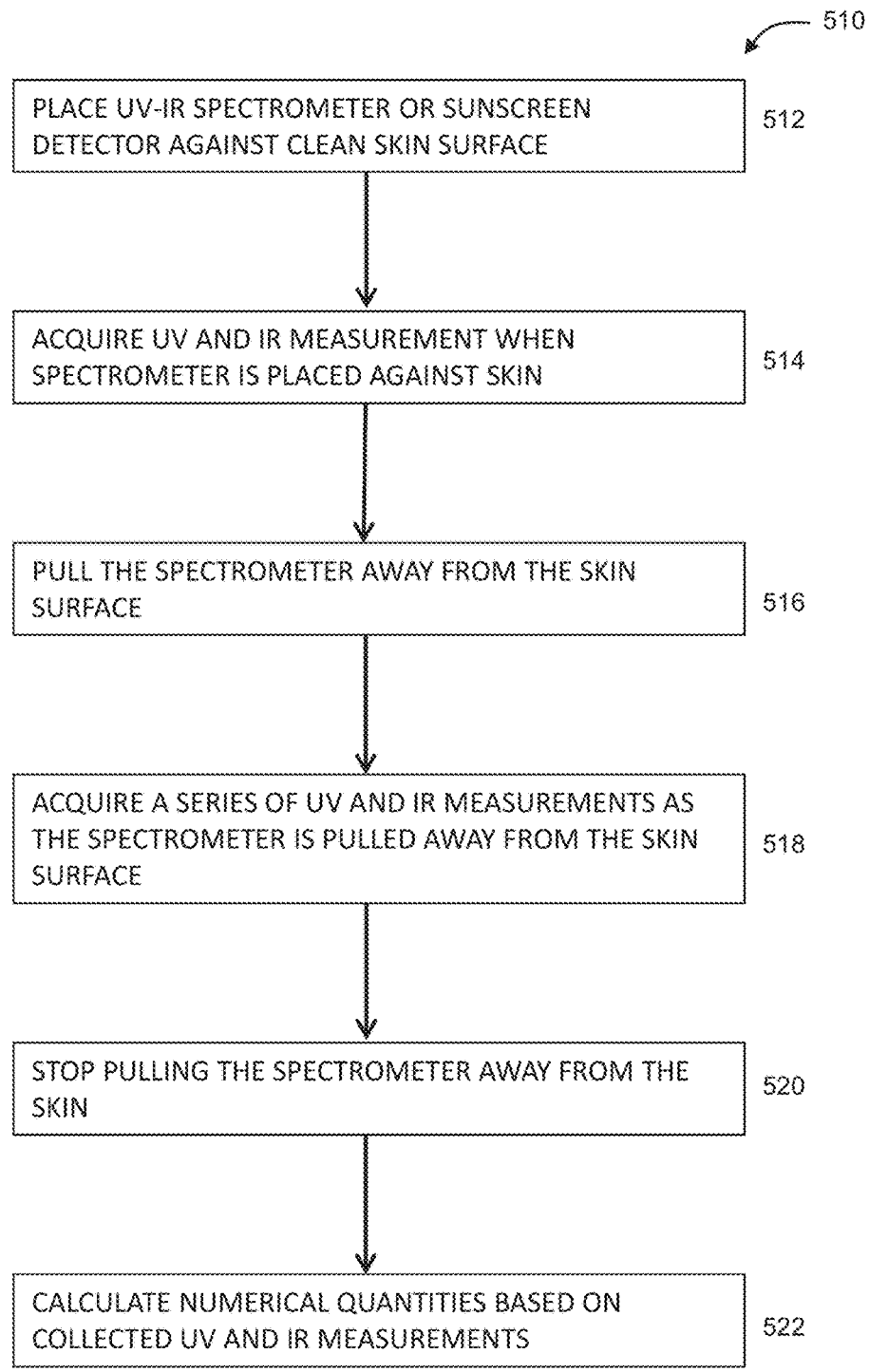
FIG. 5 is a flow diagram of one variation of a calibration protocol.

In some variations, a calibration protocol may comprise the steps depicted in FIG. 5. FIG. 5 depicts a variation of a calibration protocol that may be used, for example, to map UV or IR light reflectance from clean skin (i.e., without sunscreen) as a function of the distance between the UV-IR spectrometer or sunscreen detector and the skin. The calibration protocol 510 may comprise placing 512 the detector against clean skin (i.e., skin without sunscreen). The detector may prompt the user to select a skin region that will likely experience further sun exposure, and/or where sunscreen is intended to be applied. Optionally, the detector may prompt the user to select a skin region from a list of anatomical structures that are commonly exposed to the sun, such as the arm (e.g., forearm, upper arm), leg (e.g., calves, thighs), neck (e.g., front or back), and/or face (e.g., nose, cheek, forehead). The user may indicate to the detector which of these anatomical structures the scanned skin region is located. The detector may acquire 514 a UV and IR light measurement when the detector is placed against the selected clean skin region. The acquisition of the UV and IR measurement may comprise activating the illumination system to turn on the UV and/or IR light source, and sensing the reflected light (e.g., intensity, number of photons per unit area, and/or number of photons per unit time, etc.). The acquired UV and/or IR measurement may be stored in the controller as the initial reflectance value for that skin region. For example, the baseline skin reflectance measurement and the reference measurement may be used to compute the UV threshold and IR threshold used in the scan protocol described above. Next, the detector may prompt the user to slowly pull 516 the detector away from the skin. As the user pulls the detector away from the skin, the detector acquires 518 a series of UV and IR measurements, and correlates each light measurement with the distance the detector is from the skin at the time the measurement was taken. The detector distance from the skin may be computed based on the IR measurement, for example, by using time-of-flight principles for detection (e.g., measuring the time difference between the illumination pulse and the detected pulse). The detector may alert the user to stop pulling back 520 when the UV and/or IR light signal falls below a set threshold, and/or if a set period of time has elapsed. For example, the detector may prompt the user to stop pulling back when the UV and/or IR light signal falls below a threshold that is at least partially determined by the sensitivity of the UV and/or IR sensors. Alternatively or additionally, the detector may have a countdown timer that indicates to the user the duration of the scan time and provides some guidance to the user as to the distance that the user should cover during the pull-back scan period. For example, the detector may countdown about five seconds, and may instruct the user that during that time, the user should pull back the detector over a distance of about 12 inches, or the length of their forearm, or other such intuitive reference point. The pull-back distance may be any value, and may range from about 1 in to about 18 in, or about 3 in to about 10 in, or about 3 in to about 7 in. Alternatively or additionally, the detector may prompt the user to stop pulling back when the detector has determined that the scanned distance matches a minimum distance threshold. The detector may sound beeps at a certain frequency (e.g., one beep per second, two beeps per second, etc.) so that the user can pace their movement over the scan duration. In some variations, the detector may visually indicate (e.g., on the screen or display of the mobile or wearable device to which it is attached) the distance the user should traverse as the detector is pulled back. For example, the screen may display a first bar to represent the distance traversed by the user as they are pulling back, and a second bar that represents the total distance that should be traversed during the calibration protocol. In some variations, the screen may display an image from the mobile or wearable device camera, and prompt the user to pull back the detector from against the skin until a particular visual cue is within the visual field of the camera. For example, when the detector is positioned against the skin, the camera of the mobile or wearable device may also be pressed against the skin and provide a close-up view of the skin. As the user pulls the device back from the skin, the visual scene captured by the camera will change as the camera pans away from the skin (e.g., zooming out from the initial small patch skin to viewing a larger region of skin). When the camera controller detects one or more edges that extend across the entire visual field, that edge may be interpreted as the boundary of that body region. For example, if the skin region is located on the forearm, as the device is pulled back, the edge(s) of the arm will come into view. The detector may alert the user to stop pulling back when a particular feature in the visual scene is detected (e.g., a sufficiently long anatomical edge, or when the majority of the area of the visual scene is background subject matter and not the skin). After the user has stopped pulling back the detector from the skin, the detector may take a final UV and/or IR light measurement and then use the collected data to calculate 522 numerical quantities, coefficients, and/or thresholds that may be used by the detector to determine how much sunscreen has been applied and whether that quantity provides adequate sun protection. Examples of such numerical quantities, coefficients, and/or thresholds may include light levels used to determine whether a sunscreen has absorbed an adequate quantity of UV light, intrinsic skin light absorption and/or reflection properties, ambient light levels, and noise levels. For example, the controller may use the collected data to generate a calibration curve of the UV reflectance as a function of the detector distance so that the effect of detector distance is normalized when analyzing scan data. During use, the detector may refer to this UV-distance calibration curve to derive an UV value (e.g., an UV threshold) against which to compare the scanned UV data (and similar with the IR measurement data). In some variations, the controller of the detector may determine whether sufficient sunscreen has been applied based on a percent reduction and/or absolute reduction (e.g., in the number of photons per unit area or time) of absorbed UV light as compared to the values on the UV-distance calibration curve. Alternatively or additionally, a calibration curve of the ratio of UV light attenuation as a function of distance may be generated by plotting the ratio of the UV light data to the UV initial reflectance value (e.g., UV light data normalized to the UV initial reflectance value) for a series of points along the pullback distance.

Some variations may have a self-calibrating protocol. A self-calibrating protocol may allow the UV-IR spectrometer of the portable or wearable device to be used with different people without the person manually performing calibration steps. In addition to the light measurements that are acquired and stored during the calibration protocols described above, a calibration protocol may also prompt the user for information that may be used for identification and/or adjusting light threshold values and/or formulating recommendations on when to apply sunscreen and how much. For example, the calibration protocol may query the user regarding skin type, SPF of sunscreen to be used, age, gender, anticipated sun exposure time, etc. In some variations, such data may also be used to help select or adjust UV and IR thresholds used in the scan protocol described and depicted in FIG. 4. This data may be provided orally to the UV-IR spectrometer (e.g., by voice recognition), or may be entered using a manual input device (e.g., touch screen, keyboard, mouse), or may be obtained from a remote server where that information is stored (e.g., a cloud server). A UV-IR spectrometer may be able to store this data (along with the light measurements from the sensor system) on the local controller (e.g., the controller of the spectrometer and/or the controller of the mobile and/or wearable device that interfaces with the spectrometer), or may store this data in the cloud (wireless or USB wired connection). Any of the above calibration protocols may be repeated for multiple anatomical structures, as may be desired. Furthermore, any of the above calibration protocols may optionally include dark channel subtraction, which may help to cancel out ambient UV light. One example of dark channel subtraction may comprise repeatedly turning on and off the UV and/or IR light sources. A first measurement may be taken when the UV light is on and a second measurement may be taken when the UV light is turned off (e.g., microseconds or milliseconds after the UV light is turned off). UV and/or IR measurements taken when the light sources are off (e.g., baseline UV and/or IR light levels) may be subtracted from UV and/or IR measurements taken with the UV and/or IR light sources are on. This may help to remote any systematic and/or ambient light noise during calibration and/or scanning.

Although the data collected during the calibration protocols described above may be used for analyzing scan data, the data may also be used for assessing the skin of a user. For example, the calibration protocols may be used to measure the intrinsic ability of the skin to absorb or reflect UV light, and may be used to compute the melanin levels in, or the UV sensitivity of the user's skin. In addition to the calibration steps described above, some skin assessment protocols may also include steps to determine the susceptibility of skin to the effects of UV light. "Tolerance" to UV light may be a measure of the skin's intrinsic ability to scatter and/or reflect and/or absorb UV light, and may vary from individual to individual. In some variations, a skin assessment protocol may comprise keeping the UV-IR spectrometer or sunscreen detector at a set distance away from the target skin, and then incrementing the amount of UV light applied by the spectrometer to the skin and measuring how much UV light is reflected to the detector. Such data may be used to compute a user's UV sensitivity factor, which may then in turn affect the analysis of future scan data acquired by the spectrometer. The UV sensitivity factor may be, for example, calibrated with respect to the Fitzpatrick scale. This factor, in combination with other characteristics of the user's skin, may be included in a computer-implemented method that determines whether the user has sufficient sun protection and/or whether sunscreen should be applied. These calibration protocols may be repeated over a period of time and allow the spectrometer to track and gradual changes in the user's skin. For example, a sudden increase in skin melanin levels and an accompanying increase in detected IR light levels may indicate that the user has been subject to excessive UV exposure. The spectrometer may alert the user of this condition and encourage the user to modify their behavior to help prevent the onset of sunburn, and/or reduce the severity of sunburn.

The UV and IR light data acquired during one or more calibration procedures and/or scan procedures, along with the user skin characteristics may be transmitted to the controller of the mobile and/or wearable device with which the UV-IR spectrometer is integrated. The controller may store this data in non-transitory computer-readable media ("memory"). Optionally, this data may be accessible to other applications and computer-implemented methods stored on the memory. The accessibility of this data to other computer-implemented methods may be determined by privacy preferences set by the user. The computer-implemented methods may be generated by the manufacturer of the mobile and/or wearable device, or may be generated by a third-party entity. In some variations, the computer-implemented methods may be created by a developer using an app toolkit.

The UV-IR spectrometer or sunscreen detector may be integrated into a mobile or wearable device, such as any of the portable or wearable devices described above, or may be in a separate module that is releasable attached to a mobile or wearable device, such as any of the portable or wearable devices described above. For example, a UV-IR spectrometer may be built into the housing or body of a camera phone (e.g., a smart phone), and the location of the UV-IR spectrometer may be such that the illumination system and the sensor system are located next to the camera of the phone. In some variations, the UV-IR spectrometer may not have a UV light source, and may be configured to measure UV light from the sun that is reflected off the target skin region. The controller for the UV-IR spectrometer may also be in communication with the phone camera, and in conjunction with the phone controller, generate a composite image of the target body region with the measured UV light levels. In some variations, a composite image of the target body region may include indicia that outline the FOV of the sensor system. This composite image may be displayed to a user in real-time, which may help the user to point the UV-IR spectrometer at the desired target skin region by moving the mobile device so that the target skin region so that it is within the outline of the FOV of the sensor system. In this variation, the UV-IR spectrometer need not be moved across the target skin region during a scan sequence. Optionally, the composite image may comprise arrows that instruct the user to move the mobile device with UV-IR spectrometer in a particular direction, and/or provide feedback about the scan speed. Such composite image may be derived from either or both the forward-facing camera of the phone (e.g., to acquire images of the arms, legs, face) and the back-facing camera of the phone (e.g., to acquire images of the back). The composite image may be displayed on the phone, or may be streamed to a wearable device, e.g., a wristband or watch, for viewing by the user. In some variations, the controller may have an edge recognition algorithm that identifies edges in a visual scene captured by the camera, and may then advise the user to move the UV-IR spectrometer away from that edge so that the FOV of the sensor system is directed over the target skin region.

In some variations, the composite image may comprise a 2-D map of the target body part showing regions or spots where not enough sunscreen has been applied. The composite image may comprise a still photo, over which real-time measured UV data is overlaid. Areas of the still photo for which UV light data has been acquired may be outlined, and the magnitude of the UV light data may be represented by a fill color or pattern within the outline. The fill color or pattern may be a color scale and/or variable-intensity map, and/or a variable-density pattern map. For example, the color scale may be such that areas with adequate UV light protection may be green while areas with inadequate protection may be red, with intermediate levels of protection spectrally represented by colors between red and green. The variable-intensity map may be monochromatic, and regions having adequate UV light protection may be represented with a saturated (e.g., black, or dark) shaded region, while regions with inadequate protection may be represented with a much less saturated or white shaded region. The variable-density pattern map (patterns may include hashes, slashes, cross-hatches, dots, speckles, etc.) may represent areas of adequate coverage with high-density patterns, and areas of inadequate coverage with low-density patterns. Alternatively or additionally, the composite image may have a toggle between a first viewing mode that displays the measured UV light data, and a second viewing mode that displays where the user should apply sunscreen. For example, in the first view, the still photo may have a plurality of shaded areas with varying degrees of saturation that reflects the amount of detected UV light, and in the second view, only areas where sunscreen application is required is shaded (i.e., areas that are adequately protect from UV light are not shaded in this second view).

In some variations, the UV-IR spectrometer may be located within the body of a band or wrist-worn device (e.g., a fitness tracker and/or a watch). The band or wrist-worn device may not have a native camera unit. For example, a UV-IR spectrometer may be integrated with a watch and enclosed in the housing of the watch body, or it may be located within the wrist band. The UV-IR spectrometer may be any of the spectrometers or detectors described herein. In some variations, a UV-IR spectrometer located in a watch or on a wrist band may comprise a visible light source (e.g., an LED) as described above, which may help to guide the user as the spectrometer is scanned over a target skin region. The illumination field of the visible light source may coincide with the overlap of the illumination field of the UV light source, and/or infrared light source, and/or FOV of the sensor system. As the visible light shines on a particular skin region, the controller of the UV-IR spectrometer outputs a visual indication to the watch that conveys to the user whether sufficient sunscreen was applied to the illuminated skin region. In some variations, the UV-IR spectrometer may generate a status sound or beep as it is moved across the target body region, which the pitch or frequency of the sound may vary according to the amount of UV light that is absorbed or reflected at a particular location. Alternatively or additionally, the UV-IR spectrometer may have one or more indicator lights that may change color or pulse frequency according to the amount of UV light detected by the sensor. The indicator lights may be LEDs located on an external surface of the UV-IR spectrometer that is visible to a user, and/or the indicator lights may be displayed on the display of the wearable device.

Methods

A user may utilize the UV-IR spectrometer or sunscreen detector before, during, and/or after exposure to the sun. UV and/or IR data acquired prior to sun exposure may be used to calibrate the UV-IR spectrometer, and/or may also be used in a computer-implemented method to generate recommendations to the user regarding the SPF, quantity, and application frequency of sunscreen. Scanning the skin during sun exposure may allow a user to determine whether the ability of their sunscreen to protect against UV rays has been depleted, and accordingly, the UV-IR spectrometer may advise the user to re-apply sunscreen. Scanning the skin during sun exposure may also inform a user as to the efficacy of one sunscreen as compared to another. After sun exposure, a user may scan their skin in order to gauge whether they have been exposed to excessive UV rays. Post-exposure scans may also advise a user of early phase or onset of sunburn, so that the user may take early action to treat the symptoms of sunburn.

Figure 6A:
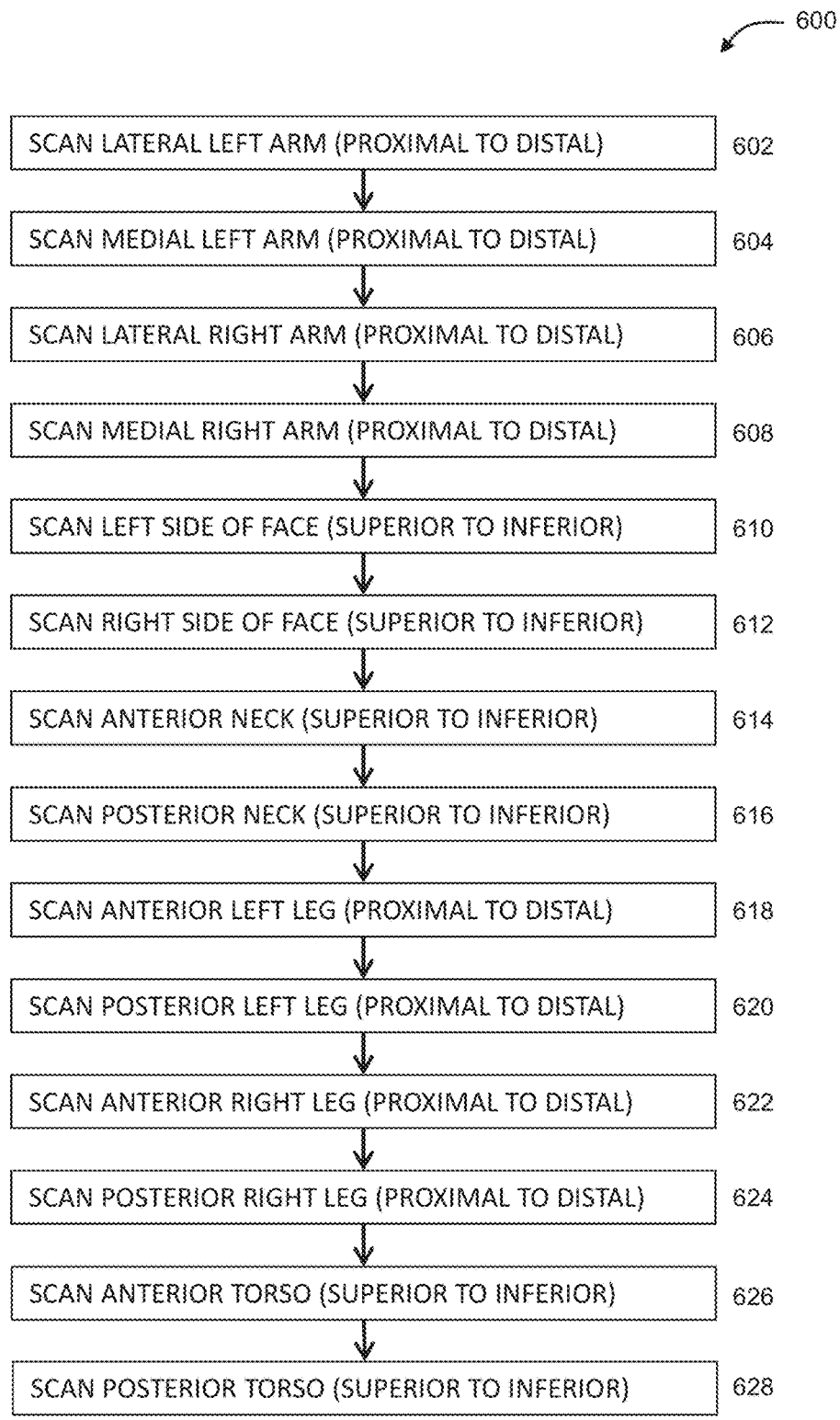
FIG. 6A is a flow diagram of one example of a method for scanning an individual with a UV-IR spectrometer.

One example of a method of using any of the UV-IR spectrometers or sunscreen detectors described herein to scan a user's skin is depicted in the flow diagram of FIG. 6A. The body regions that may be scanned and the example scan directions in this example method are represented by the schematic human outline 650 in FIG. 6B. Although this method comprises scanning multiple body regions, it should be understood that fewer body regions may be scanned (e.g., only arms, only legs, only face, only neck, and/or only arms and legs, only arms and face, only legs and face, only arms and neck, only legs and neck, only neck and face, etc.). The user may select or identify which body regions to scan, either prior to scanning or during the scanning procedure. In other variations, the user may identify what items of clothing are being worn or otherwise identified, and the software may provide a default set of scan regions corresponding to the clothing identified. Where sun exposure of additional body regions is anticipated (e.g., shoulders, back, torso, gluteal region, etc.), the method may be expanded to include those regions. The order in which body regions are scanned may also be varied. Method 600 may comprise positioning the UV-IR spectrometer over a proximal portion of the lateral portion of the left arm and then moving the spectrometer across the lateral portion of the left arm from the proximal portion to a distal region (602) in the direction of arrow 603. The UV-IR spectrometer may be positioned over a proximal portion of the medial portion of the left arm and then moved across the medial portion of the left arm from the proximal portion to a distal portion (604) in the direction of arrow 603. These steps may be repeated for the lateral portion of the right arm (606) in the direction of arrow 605 and medial portion of the right arm (608) in the direction of arrow 605. The method 600 may also comprise scanning the left side of the user's face by positioning the UV-IR spectrometer over a superior portion of the left side of a user's face and moving the spectrometer down the face (610) in the direction of arrow 611, and then scanning the right side of the user's face by positioning the UV-IR spectrometer over a superior portion of the right side of a user's face and moving the spectrometer down the face (612) in the direction of arrow 611. Alternatively, the superior half and the inferior half of the user's face may be scanned by moving the spectrometer horizontally from left to right. The anterior portion of the user's neck may be scanned (614) by positioning the spectrometer at a superior portion of the anterior portion of the neck and moving it downward to the inferior portion of the neck in the direction of arrow 607. The posterior portion of the user's neck may be scanned (616) by positioning the spectrometer at a superior portion of the neck and moving it downward to the inferior portion of the neck in the direction of arrow 607. The method 600 may also comprise scanning the anterior portion of the left leg (618) by positioning the spectrometer over a proximal portion of the anterior left leg and moving it distally in the direction of arrow 609, and scanning the posterior portion of the left leg (620) by positioning the spectrometer over a proximal portion of the posterior left leg and moving it distally in the direction of arrow 609. The method 600 may also comprise scanning the anterior portion of the right leg (622) by positioning the spectrometer over a proximal portion of the anterior right leg and moving it distally in the direction of arrow 611, and scanning the posterior portion of the right leg (624) by positioning the spectrometer over a proximal portion of the posterior right leg and moving it distally in the direction of arrow 611. The leg scans may be from the knee to the foot or ankle, and/or from the thigh to the foot or ankle (e.g., mid-thigh to the foot or ankle, upper thigh to the foot or ankle). Method 600 may optionally comprise scanning the anterior portion of the torso (626) by positioning the spectrometer over a superior portion of the torso and moving it inferiorly, in the direction of arrow 613, and scanning the posterior portion (e.g., back) of the torso (628) by positioning the spectrometer over a superior portion of the torso and moving it inferiorly, in the direction of arrow 613.

Figure 6B:
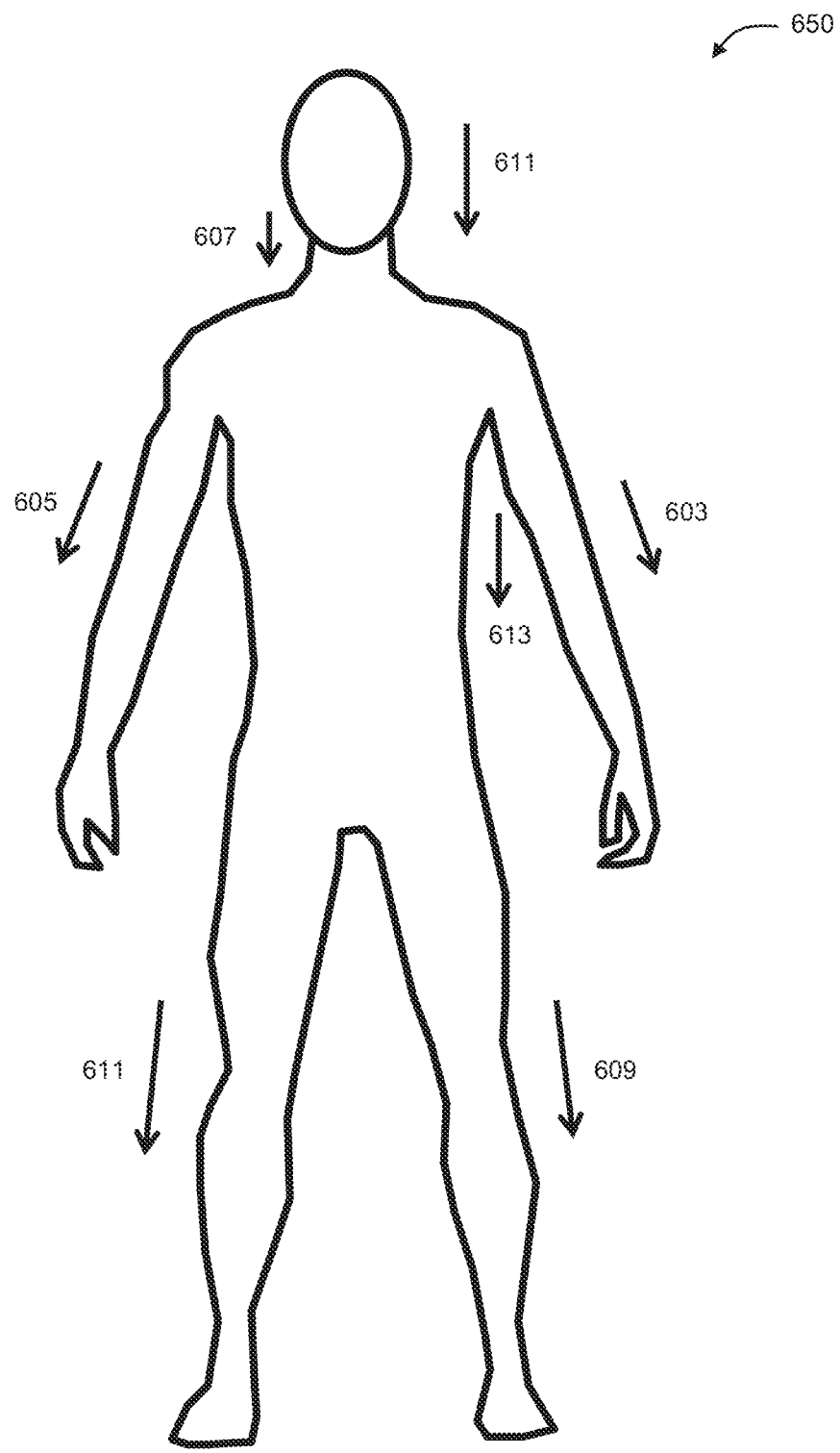
FIG. 6B is a schematic of body regions that may be scanned.

Scan steps in the method depicted in FIGS. 6A and 6B may be reduced by adjusting the FOV of the UV-IR spectrometer to be larger so that the UV and/or IR reflectance properties of multiple body regions may be captured simultaneously. For example, with a sufficiently large FOV, e.g., where the size of the FOV is from about 80 to 1500 $cm^2$ at a distance of 5 cm from the sensor system, the UV and/or IR reflectance data for the face may be obtain in one pass or scan, instead of scanning each of the face sequentially. Increasing the FOV may also reduce the amount of movement of the spectrometer across the length of a body region. For example, the UV-IR spectrometer may be placed halfway along the length of an arm (e.g., at or near the elbow) and UV and/or IR data may be acquired for the entire length of the arm if the area of the FOV is from about 900 $cm^2$ at a distance of 5 cm from the sensor system.

Although the variations herein have been described in relation to certain examples, various additional variations and alterations to the described examples are contemplated within the scope of the invention. Thus, no part of the foregoing description should be interpreted to limit the scope of the invention as set forth in the following claims. For all of the variations described above, the steps of the methods need not be performed sequentially. The foregoing description, for purpose of explanation, has been described with reference to specific variations. However, the illustrative discussions above are not intended to be exhaustive or to limit the invention to the precise forms disclosed. Many modifications and variations are possible in view of the above teachings. The variations were chosen and described in order to best explain the principles of the techniques and their practical applications. Others skilled in the art are thereby enabled to best utilize the techniques and various variations with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

In some variations, the technologies described above may include the acquisition of information from a variety of sources, which may or may not include personalized information that may identify some aspect of the user, or which could be used with additional information to uniquely identify the user or some aspect of user behavior. This information may include, for example, email addresses, phone numbers, physical addresses, demographic data, search history, location information, biometric information, health information, and other user-related information.

In certain embodiments described herein, the use of personalized or user-related information may be used to provide certain functionality or other useful features to the users. This may include providing content to the user that is tailored or targeted at subject matter that may be greater interest, based upon location or search history, for example. Thus, in some variations, the personalized or user-related information may be utilized to determine or adjust the nature or scope of content provided to the user, in addition to other user benefits as contemplated in view of the above.

In the various embodiments described herein, the use and/or control of the personalized or user-related information, including but not limited to biometric data and health information, will managed or handled in accordance to well-established user privacy policies and practices of the appropriate jurisdictions. This includes the receipt, transmission, storage, analysis, aggregation and disclosure of such information. The management of this information by the appropriate entities will be in accordance with privacy policies and practices that are generally known to comply with or exceed the established policies and practices, as recognized for the relevant industry or government requirements for data privacy and data security. For example, personalized information from users may be collected for reasonable and permitted uses and may not be shared or sold outside of such uses. Also, the receipt, storage and use of such information will occur only after receiving the informed consent of the users. The procedures for securing and safeguard the personalized user information will be implemented so that others accessing the information will also comply with the data privacy and security policies and practices. The access and use of such information will be such that adherence to well-known privacy policies and practices may be determined or certified by third parties.

In view of the above, in some embodiments, one or more uses may selectively limit or restrict the use of certain personalized information and biometric for related product features or services. This may occur through hardware and/or software controls provided to the user. In one example, the user may selectively turn on or turn off location information that may be used to provide user-specific content. In a further example, the user is able to selectively set the degree of precision or detail in the information collected, e.g. the general location via wireless connectivity points selectable by the user, or by zip code or city, for example. In another example, in the delivery of advertising content to a user, the various embodiments may be configured to permit the user to opt-out or opt-in to the collection of user information, either during the initial registration of the product, or at others times via a control setting.

In still other examples, the user may be prompted to enter manual location information or other information to provide targeted content delivery, while in other examples, it is contemplated that the various product features and services may be also provided without the need or use of personalized user information. Thus, where no personalized user information is provided or permitted for use, the content may be provided generically, or otherwise determined or derived based upon non-personal, generic or publicly available information, without rendering that feature or service unavailable to the user.

A sunscreen detector is disclosed. In some examples, the sunscreen detector can comprise: an illumination system configured to emit UV light, included in a UV illumination field, and IR light, included in an IR illumination field; a sensor system, the sensor system configured to: detect at least a portion of the UV light and the IR light at a sensor field located within the UV illumination field and the IR illumination field, generate a UV signal associated with the detected UV light, and generate an IR signal associated with the detected IR light; and a controller configured to: receive the UV signal and the IR signal from the sensor system, compare the UV signal to a UV threshold, compare the IR signal to an IR threshold, and output a first output signal when the IR signal is above the IR threshold and the UV signal is below the UV threshold. Additionally or alternatively, in some examples, wherein the sensor system comprises an optic to limit the sensor field. Additionally or alternatively, in some examples, the sensor field has an area in the range of 0.1 to 1500 $cm^2$ at a distance of 5 cm from the sensor system. Additionally or alternatively, in some examples, the sensor field has an area in the range of 5 to 20 $cm^2$ at a distance of 5 cm from the sensor system. Additionally or alternatively, in some examples, the controller is further configured to: overlay a graphic corresponding to the sensor field onto a camera image, and output a second output signal when the IR signal is above the IR threshold and the UV signal is above the UV threshold, wherein the graphic is a second graphic corresponding to the second output signal. Additionally or alternatively, in some examples, the controller is further configured to: overlay a graphic corresponding to the sensor field onto a camera image, and output a third output signal when the IR signal is below the IR threshold, wherein the graphic is a third graphic corresponding to the third output signal. Additionally or alternatively, in some examples, the illumination system is further configured to emit visible light. Additionally or alternatively, in some examples, further comprising a distance sensor system configured to detect a distance of an object in the sensor field from the distance sensor system.

A method for detecting sunscreen coverage is disclosed. The method can comprise: positioning a detector over a target skin region; moving the detector across the target skin region; emitting UV light and IR light; detecting at least a portion of the emitted UV light and the emitted IR light at a sensor field located within a UV illumination field and an IR illumination field; generating a UV signal indicative of the detected UV light; generating an IR signal indicative of the detected IR light; receiving the UV signal and the IR signal from the sensor system; comparing the IR signal to an IR threshold value; comparing the UV signal to a UV threshold value; outputting an output signal based on the comparisons; and generating an alert based on the output signal. Additionally or alternatively, in some examples, the method further comprises: displaying the alert, the alert including an instruction to apply sunscreen over the target skin region, when the IR signal is above the IR threshold and the UV signal is above the UV threshold value. Additionally or alternatively, in some examples, the method further comprises: acquiring an image that includes the target skin region; and displaying a composite image that comprises a graphic of the sensor field overlaid over the image. Additionally or alternatively, in some examples, the output signal includes an indication that that the target skin region has sufficient sunscreen coverage when the IR signal is above the IR threshold and the UV signal is below the UV threshold. Additionally or alternatively, in some examples, the output signal includes an indication that the target skin region is to be re-measured when the IR signal is below the IR threshold. Additionally or alternatively, in some examples, the method further comprising: emitting visible light towards the target skin region to guide the moving of the detector. Additionally or alternatively, in some examples, the method further comprising: calibrating the detector, the calibration comprising: scanning a skin region that has no sunscreen to acquire a baseline UV light measurement and a baseline IR light measurement; and scanning a reflective surface to acquire a reference UV light measurement and a reference IR light measurement. Additionally or alternatively, in some examples, the method further comprises: calibrating the detector, the calibration comprising: placing the detector against a skin region that has no sunscreen, acquiring a first measurement comprising a UV light level and an IR light level, pulling the detector away from the skin region, acquiring a plurality of measurements while pulling the detector away from the skin region, each of the plurality of measurements comprising a UV light level, an IR light level, and a distance between the detector and the skin region; and calculating the UV threshold and the IR threshold based on the plurality of measurements. Additionally or alternatively, in some examples, the detector is pulled back over a distance of about 1 in to about 18 in. Additionally or alternatively, in some examples, the controller is configured to determine melanin levels in the skin region based on the plurality of measurements. Additionally or alternatively, in some examples, calculating the UV threshold and IR threshold comprises calculating a ratio of the UV light level of each of the plurality of measurements to the UV light level of the first measurement. Additionally or alternatively, in some examples, the method further comprises determining one or more of a presence and location of the target skin region based on the IR signal.

The invention claimed is:

1. A sunscreen detector, comprising:
 an illumination system configured to emit UV light, included in a UV illumination field, and IR light, included in an IR illumination field;
 a sensor system, the sensor system configured to:
  detect at least a portion of the UV light and the IR light at a sensor field located within the UV illumination field and the IR illumination field,
  generate a UV signal associated with the detected UV light, and
  generate an IR signal associated with the detected IR light; and
 a controller configured to:
  receive the UV signal and the IR signal from the sensor system,
  compare the UV signal to a UV threshold,
  compare the IR signal to an IR threshold, and
  output a first output signal when the IR signal is above the IR threshold and the UV signal is below the UV threshold.

2. The sunscreen detector of claim 1, wherein the sensor system comprises an optic to limit the sensor field.

3. The sunscreen detector of claim 2, wherein the sensor field has an area in the range of 0.1 to 1500 cm$^2$ at a distance of 5 cm from the sensor system.

4. The sunscreen detector of claim 2, wherein the sensor field has an area in the range of 5 to 20 cm$^2$ at a distance of 5 cm from the sensor system.

5. The sunscreen detector of claim 1, wherein the controller is further configured to:
 overlay a graphic corresponding to the sensor field onto a camera image, and
 output a second output signal when the IR signal is above the IR threshold and the UV signal is above the UV threshold,
 wherein the graphic is a second graphic corresponding to the second output signal.

6. The sunscreen detector of claim 1, wherein the controller is further configured to:
 overlay a graphic corresponding to the sensor field onto a camera image, and
 output a third output signal when the IR signal is below the IR threshold,
 wherein the graphic is a third graphic corresponding to the third output signal.

7. The sunscreen detector of claim 1, wherein the illumination system is further configured to emit visible light.

8. The sunscreen detector of claim 1, further comprising a distance sensor system configured to detect a distance of an object in the sensor field from the distance sensor system.

9. A method for detecting sunscreen coverage, comprising:
 positioning a detector over a target skin region;
 moving the detector across the target skin region;
 emitting UV light and IR light;
 detecting at least a portion of the emitted UV light and the emitted IR light at a sensor field located within a UV illumination field and an IR illumination field;
 generating a UV signal indicative of the detected UV light;
 generating an IR signal indicative of the detected IR light;
 receiving the UV signal and the IR signal from the sensor system;
 comparing the IR signal to an IR threshold value;
 comparing the UV signal to a UV threshold value;
 outputting an output signal based on the comparisons; and
 generating an alert based on the output signal.

10. The method of claim 9, further comprising:
 displaying the alert, the alert including an instruction to apply sunscreen over the target skin region, when the IR signal is above the IR threshold and the UV signal is above the UV threshold value.

11. The method of claim 9, further comprising:
 acquiring an image that includes the target skin region; and
 displaying a composite image that comprises a graphic of the sensor field overlaid over the image.

12. The method of claim 9, wherein the output signal includes an indication that that the target skin region has sufficient sunscreen coverage when the IR signal is above the IR threshold and the UV signal is below the UV threshold.

13. The method of claim 9, wherein the output signal includes an indication that the target skin region is to be re-measured when the IR signal is below the IR threshold.

14. The method of claim 9, further comprising:
 emitting visible light towards the target skin region to guide the moving of the detector.

15. The method of claim 9, further comprising:
 calibrating the detector, the calibration comprising:
 scanning a skin region that has no sunscreen to acquire a baseline UV light measurement and a baseline IR light measurement; and
 scanning a reflective surface to acquire a reference UV light measurement and a reference IR light measurement.

16. The method of claim 9, further comprising:
 calibrating the detector, the calibration comprising:
 placing the detector against a skin region that has no sunscreen,
 acquiring a first measurement comprising a UV light level and an IR light level,
 pulling the detector away from the skin region,
 acquiring a plurality of measurements while pulling the detector away from the skin region, each of the plurality of measurements comprising a UV light level, an IR light level, and a distance between the detector and the skin region; and
 calculating the UV threshold and the IR threshold based on the plurality of measurements.

17. The method of claim 16, wherein the detector is pulled back over a distance of about 1 in to about 18 in.

18. The method of claim 16, wherein the controller is configured to determine melanin levels in the skin region based on the plurality of measurements.

19. The method of claim 16, wherein calculating the UV threshold and IR threshold comprises calculating a ratio of the UV light level of each of the plurality of measurements to the UV light level of the first measurement.

20. The method of claim 9, further comprising determining one or more of a presence and location of the target skin region based on the IR signal.

\* \* \* \* \*